(12) United States Patent
Simoneau et al.

(10) Patent No.: US 7,569,723 B2
(45) Date of Patent: Aug. 4, 2009

(54) BENZOIC ACID DERIVATIVES AS NON NUCLEOSIDE REVERSE-TRANSCRIPTASE INHIBITORS

(75) Inventors: Bruno Simoneau, Laval (CA); Jeffrey O'Meara, Boisbriand (CA); Christiane Yoakim, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 12/014,185

(22) Filed: Jan. 15, 2008

(65) Prior Publication Data

US 2008/0114068 A1 May 15, 2008

Related U.S. Application Data

(63) Continuation of application No. 11/184,689, filed on Jul. 19, 2005, now abandoned.

(60) Provisional application No. 60/598,227, filed on Aug. 2, 2004.

(51) Int. Cl.
*C07C 229/08* (2006.01)
*A61K 31/195* (2006.01)

(52) U.S. Cl. .................. 562/450; 564/181; 564/184; 514/563; 514/621

(58) Field of Classification Search ............ 564/181, 564/184; 514/563, 621; 562/450
See application file for complete search history.

(56) References Cited

U.S. PATENT DOCUMENTS

2004/0122064 A1    6/2004   Chan

FOREIGN PATENT DOCUMENTS

| CA | 2383782    |    | 3/2001  |
|----|------------|----|---------|
| EP | 1438973    | A1 | 7/2004  |
| WO | 0117982    | A1 | 3/2001  |
| WO | 0196338    | A1 | 12/2001 |
| WO | 02070470   | A2 | 9/2002  |
| WO | 03075907   | A2 | 9/2003  |
| WO | 2004009533 | A1 | 1/2004  |
| WO | 2004050643 | A2 | 6/2004  |

OTHER PUBLICATIONS

Berge, et al; Pharmaceutical Salts; Journal of Pharmaceutical Science; Jan. 1977; vol. 66; No. 1; pp. 1-19.

Wyatt, et al: Benzophenone Derivatives: A Novel Series of Potent and Selective Inhibitors of Human Immunodeficiency Virus Type 1 Reverse Transcriptase; J. Med. Chem.; 1995; vol. 38; pp. 1657-1665; American Chemical Society.

Chan, et al; Novel Benzophenones as Non-nucleoside Reverse Transcriptase Inhibitors of HIV-1; J. Med. Chem.; 2004; vol. 47; pp. 1175-1182; American Chemical Society.

Nader, et al; Synthesis of [carbonyl-11C]2-(2-benzoylphenoxy)-N-phenylacetamide from [11C]carbon monoxide by the Suzuki and the Stille reactions; Applied Radiation and Isotopes; 2002; vol. 57; pp. 681-685; Pergamon.

Balzarini, J.; Current Status of the Non-nucleoside Reverse Transcriptase Inhibitors of Human Immunodeficiency Virus Type 1; Current Topics in Medicinal Chemistry; May 2004; vol. 4(9); pp. 921-944.

De Clercq; The role of non-nucleoside reverse transcriptase inhibitors (NNRTIs) in the therapy of HIV-1 infection; Antiviral Research; 1998; vol. 38; pp. 153-179.

Pauwels; new non-nucleoside reverse transcriptase inhibitors (NNRTIs) in development for the treatment of HIV infections; Current Opinion in Pharmacology, Web Release: Aug. 24, 2004; pp. 437-446.

Pedersen, et al; Non-nucleoside reverse transcriptase inhibitors: the NNRTI boom; Antiviral Chemistry & Chemotherapy; 1999; vol. 10; pp. 285-314.

Andries, et al; TMC125, a novel next generation nonnucleoside reverse transcriptase inhibitor active against nonnucleoside reverse transcriptase inhibitor-resistant human immunodeficiency virus type 1; Antimicrobial Agents & Chemotherapy; Dec. 2004; vol. 48 (12); pp. 4680-4686.

*Primary Examiner*—Shailendra Kumar
(74) *Attorney, Agent, or Firm*—Michael P. Morris; Mary-Ellen M. Devlin; Alan R. Stempel

(57) ABSTRACT

Compounds of formula (I):

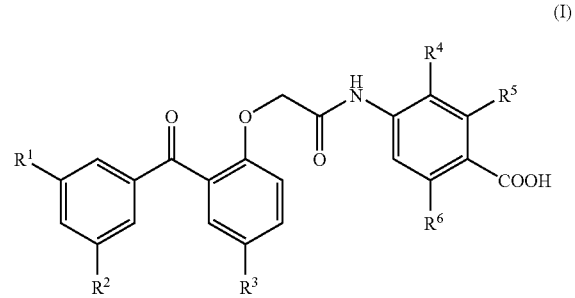

wherein $R^1$, $R^2$, $R^3$, $R^4$, $R^5$ and $R^6$ are as defined herein. The compounds are useful as reverse transcriptase inhibitors against HIV. In particular, the compounds are active against wild type and single or double mutant strains of HIV.

16 Claims, No Drawings

BENZOIC ACID DERIVATIVES AS NON NUCLEOSIDE REVERSE-TRANSCRIPTASE INHIBITORS

RELATED APPLICATIONS

This application is a continuation of U.S. Ser. No. 11/184,689, filed Jul. 19, 2005, now abandoned, and claims benefit, as does the present application, of U.S. Ser. No. 60/598,227, filed Aug. 2, 2004.

TECHNICAL FIELD OF THE INVENTION

The invention relates to novel compounds which inhibit HIV reverse transcriptase, a method for the treatment of HIV infection using the compounds, and pharmaceutical compositions comprising the compounds.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes copies of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as zidovudine, didanosine, zalcitabine, stavudine, lamivudine, emtricitabine, abacavir, tenofovir, nevirapine, delavirdine and efavirenz, the main reverse transcriptase inhibitors thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. One of the more commonly observed mutants clinically for the non-nucleoside reverse transcriptase inhibitors is the K103N mutant, in which a lysine (K), at codon 103, has been mutated to a asparagine (N) residue. Other mutants, which emerge with varying frequency during treatment using known antivirals, include single mutants Y181C, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Antiviral entry inhibitors useful in treating HIV infection have been described in WO 03/075907 (Tibotec) and non-nucleoside inhibitors of HIV reverse transcriptase containing a benzophenone moiety have been described in WO 01/17982 (Glaxo) and WO 02/070470 (SmithKline Beecham). As well, non-nucleoside inhibitors of HIV reverse transcriptase have been described in WO 2004/050643 (Boehringer Ingelheim).

The present invention provides novel compounds which show potent activity against wild type HIV reverse transcriptase as well as against single mutant and double mutant strains.

SUMMARY OF THE INVENTION

The invention provides compounds of formula (I) which are useful for treating HIV infection in a human infected by HIV. The compounds are potent inhibitors of wild-type (WT) and double mutant strains of HIV-1 RT, particularly the double mutant K103N/Y181C.

In a first aspect the invention provides a compound, represented by formula (I):

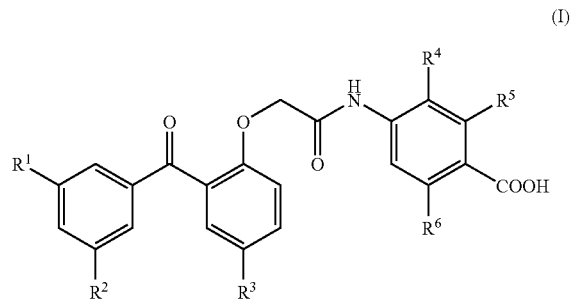

wherein
$R^1$ and $R^2$ are each independently selected from H, halo, cyano, $(C_{1-4})$alkyl, $(C_{1-4})$haloalkyl, $(C_{2-4})$alkenyl, $(C_{2-4})$alkynyl and $(C_{3-6})$cycloalkyl;
with the proviso that when $R^1$ is H, $R^2$ cannot be H;
$R^3$ is halo;
$R^4$ is selected from $(C_{1-4})$alkyl, halo and nitro; and
$R^5$ and $R^6$ are each independently selected from H, halo and $(C_{1-4})$alkyl; or a salt thereof.

According to a further aspect of the invention, there is provided a pharmaceutical composition, comprising a compound of formula (I) as defined hereinbefore and hereinafter, or a pharmaceutically acceptable salt thereof, and optionally one or more pharmaceutically acceptable carriers.

According to yet another aspect of the invention, there is provided a pharmaceutical composition, comprising a compound of formula (I) as defined hereinbefore and hereinafter, or a pharmaceutically acceptable salt thereof, in combination with one or more other antiretroviral drugs.

According to another aspect of the invention, there is provided a pharmaceutical composition for the treatment of HIV infection, comprising a compound of formula (I) as defined hereinbefore and hereinafter, or a pharmaceutically acceptable salt thereof, and optionally one or more pharmaceutically acceptable carriers.

A further aspect of the invention provides a pharmaceutical composition for the treatment of HIV infection, comprising a compound of formula (I) as defined hereinbefore and hereinafter, or a pharmaceutically acceptable salt thereof, and optionally one or more pharmaceutically acceptable carriers, in combination with one or more other antiretroviral drugs.

Another important aspect of the invention involves a method of treating an HIV infection in a mammal by administering to the mammal an anti-HIV effective amount of a compound of formula (I) as defined hereinbefore and hereinafter, a pharmaceutically acceptable salt thereof, or a composition as described above, alone or in combination with at least one other antiretroviral agent, administered together or separately.

Still another aspect of the invention provides the use of a compound of formula (I) as defined hereinbefore and hereinafter, or a pharmaceutically acceptable salt thereof, for the treatment of HIV infection in a mammal.

According to another aspect of the invention, there is provided a method of inhibiting HIV-1 replication by exposing the virus to an inhibitory amount of a compound of formula (I) as defined hereinbefore and hereinafter, or a pharmaceutically acceptable salt thereof.

Yet another aspect of the invention provides the use of a compound of formula (I) as defined hereinbefore and hereinafter, or a pharmaceutically acceptable salt thereof, to inhibit HIV-1 replication.

According to another aspect of the invention, there is provided the use of a compound of formula (I) as defined hereinbefore and hereinafter, or a pharmaceutically acceptable salt thereof, for the manufacture of a medicament for the treatment of an HIV infection.

According to yet another aspect of the invention, there is provided the use of a compound of formula (I) as defined hereinbefore and hereinafter, or a pharmaceutically acceptable salt thereof, for the manufacture of a medicament for the treatment of an HIV infection, in combination with one or more other antiretroviral drugs.

Another aspect of the invention provides an article of manufacture comprising a composition effective to treat an HIV infection or to inhibit the reverse transcriptase of HIV; and packaging material comprising a label which indicates that the composition can be used to treat infection by the human immunodeficiency virus; wherein the composition comprises a compound of formula (I) as defined hereinbefore and hereinafter, or a pharmaceutically acceptable salt thereof.

DETAILED DESCRIPTION OF THE INVENTION

Definitions

The following definitions apply unless otherwise noted:

As used herein, the term "$(C_{1-n})$alkyl" wherein n is an integer, either alone or in combination with another radical, is intended to mean acyclic straight or branched chain alkyl radicals containing from one to n carbon atoms respectively. Examples of such radicals include, but are not limited to, methyl (Me), ethyl (Et), propyl (Pr), 1-methylethyl (iPr), butyl (Bu), 1-methylpropyl, 2-methylpropyl (iBu), and 1,1-dimethylethyl (tBu), wherein the abbreviations commonly used herein are given in brackets.

As used herein, the terms "halo" or "halogen", used interchangeably, mean a halo radical selected from bromo, chloro, fluoro or iodo.

As used herein, the term "$(C_{1-n})$haloalkyl" wherein n is an integer, means an alkyl radical containing one to n carbon atoms wherein one or more hydrogen atoms are replaced by a halogen atom (including but not limited to trifluoromethyl).

As used herein, the term "$(C_{2-n})$alkenyl" wherein n is an integer, either alone or used with another radical, means an unsaturated, acyclic, straight or branched chain radical containing two to n carbon atoms, at least two of which are bonded to each other by a double bond and includes, but is not limited to, $-CH=CH_2$, $-CH_2CH=CH_2$, $-CH_2CH=CHCH_3$ and $-CH(Me)CH=CH_2$. The cis and trans isomers, and mixtures thereof, of the $(C_{2-n})$ alkenyl radical are encompassed by the term. A $(C_{2-n})$alkenyl radical may be substituted on any of the carbon atoms thereof which would otherwise bear a hydrogen atom.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. A $(C_{2-n})$alkynyl radical may be substituted on any of the carbon atoms thereof which would otherwise bear a hydrogen atom.

The term "$(C_{3-m})$cycloalkyl" as used herein, wherein m is an integer, either alone or in combination with another substituent, means a cycloalkyl substituent containing from 3 to m carbon atoms and includes, but is not limited to, cyclopropyl (cPr), cyclobutyl (cBu), cyclopentyl, cyclohexyl and cycloheptyl, wherein the abbreviations commonly used herein are given in brackets.

As used herein, the term "inhibitor of HIV replication" refers to an agent capable of reducing or eliminating the ability of HIV-1 reverse transcriptase to replicate a DNA copy from an RNA template.

As used herein, the term "single or double mutant strains" means that either one or two amino acid residues that are present in WT HIV-1 strain have been replaced by residues not found in the WT strain. For example, for the single mutant Y181C, the tyrosine at residue 181 of the wild type HIV reverse transcriptase enzyme has been replaced by a cysteine residue. Similarly, for the double mutant K103N/Y181C, an asparagine residue has replaced the lysine at residue 103 of the wild type HIV reverse transcriptase enzyme and a cysteine residue has replaced the tyrosine at residue 181.

The term "salt thereof" means any base addition salt of a compound according to the invention; preferably a pharmaceutically acceptable salt thereof.

As used herein, the term "pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

As used herein, the term "treatment" means the administration of a compound or composition according to the present invention to alleviate or eliminate symptoms of the HIV disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV-1 from mother to baby, by administration to the mother before giving birth and to the child within the first days of life The following sign ⊤ is used in sub-formulas to indicate the bond which is connected to the rest of the molecule as defined.

DETAILED DESCRIPTION OF PREFERRED EMBODIMENTS

In the following preferred embodiments, groups and substituents of the compounds of formula (I) according to this invention are described in detail.

$R^1$ and $R^2$:

Preferably, $R^1$ and $R^2$ are each independently selected from H, halo, cyano, $(C_{1-4})$alkyl, $(C_{1-4})$haloalkyl, and $(C_{3-6})$cycloalkyl;
with the proviso that when $R^1$ is H, $R^2$ cannot be H.

More preferably, $R^1$ and $R^2$ are each independently selected from H, fluoro, chloro, bromo, iodo, cyano, methyl, trifluoromethyl and cyclopropyl;
with the proviso that when $R^1$ is H, $R^2$ cannot be H.

Most preferably, $R^1$ and $R^2$ are each independently selected from H, fluoro, chloro, bromo, cyano, trifluoromethyl and cyclopropyl;
with the proviso that when $R^1$ is H, $R^2$ cannot be H.

Any and each individual definition of $R^1$ and $R^2$ as set out herein may be combined with any and each individual definition of $R^3$, $R^4$, $R^5$ and $R^6$ as set out herein.

$R^3$:

Preferably, $R^3$ is chloro.

Any and each individual definition of $R^3$ as set out herein may be combined with any and each individual definition of $R^1$, $R^2$, $R^4$, $R^5$ and $R^6$ as set out herein.

$R^4$:

Preferably, $R^4$ is selected from chloro, bromo, nitro and methyl.

More preferably, $R^4$ is chloro, bromo or methyl.

Any and each individual definition of $R^4$ as set out herein may be combined with any and each individual definition of $R^1$, $R^2$, $R^3$, $R^5$ and $R^6$ as set out herein.

$R^5$:

Preferably, $R^5$ is H, fluoro, chloro or methyl.

More preferably, $R^5$ is H or fluoro.

Alternatively more preferably, $R^5$ is fluoro, chloro or methyl.

Any and each individual definition of $R^5$ as set out herein may be combined with any and each individual definition of $R^1$, $R^2$, $R^3$, $R^4$ and $R^6$ as set out herein.

$R^6$:

Preferably, $R^6$ is H or fluoro.

More preferably, $R^6$ is H.

Any and each individual definition of $R^6$ as set out herein may be combined with any and each individual definition of $R^1$, $R^2$, $R^3$, $R^4$ and $R^5$ as set out herein.

In one embodiment is provided a compound of formula (I):

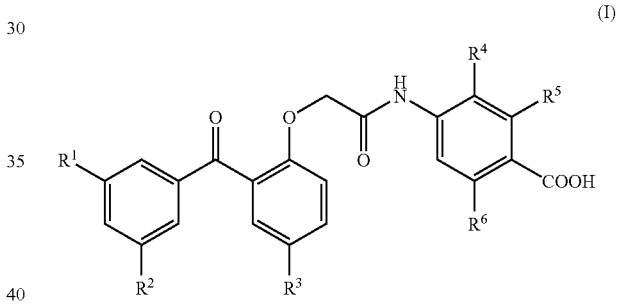

(I)

wherein
$R^1$ and $R^2$ are each independently selected from H, halo, cyano, $(C_{1-4})$alkyl, $(C_{2-4})$alkenyl, $(C_{2-4})$alkynyl and $(C_{3-6})$cycloalkyl; wherein said $(C_{1-4})$alkyl is optionally substituted with one to three halo substituents;
with the proviso that when $R^1$ is H, $R^2$ cannot be H;
$R^3$ is halo;
$R^4$ is selected from $(C_{1-4})$alkyl, halo and nitro;
$R^5$ is selected from H and halo; and
$R^6$ is H;

or a pharmaceutically acceptable salt thereof.

A preferred embodiment of the invention provides a compound of formula (I) wherein
$R^1$ and $R^2$ are each independently selected from H, halo, cyano, $(C_{1-4})$alkyl, $(C_{1-4})$haloalkyl, and $(C_{3-6})$cycloalkyl;
with the proviso that when $R^1$ is H, $R^2$ cannot be H;
$R^3$ is chloro;
$R^4$ is chloro, bromo, nitro or methyl;
$R^5$ is H, fluoro, chloro or methyl; and
$R^6$ is H or fluoro.

A more preferred embodiment of the invention provides a compound of formula (I) wherein
$R^1$ and $R^2$ are each independently selected from H, fluoro, chloro, bromo, cyano, trifluoromethyl and cyclopropyl;

with the proviso that when $R^1$ is H, $R^2$ cannot be H;
$R^3$ is chloro;
$R^4$ is chloro, bromo or methyl;
$R^5$ is H, fluoro, chloro or methyl; and
$R^6$ is H or fluoro.

Specific Embodiments

Included within the scope of this invention is each single compound of formula (I) as presented in Table 1.

The compounds of formula (I) are effective inhibitors of wild type HIV as well as of the double mutant reverse transcriptase enzyme K103N/Y181C. The compounds of the invention may also inhibit the single mutant enzymes V106A, Y188L, K103N, Y181C, P236L and G190A (among others). The compounds may also inhibit other double mutant enzymes including K103N/P225H, K103N/V108I and K103N/L100I.

The compounds of formula (I) possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a compound of formula (I), as described above. The compounds may also be used to prevent perinatal transmission of HIV-1 from mother to baby, by administration to the mother before giving birth and to the child within the first days of life.

The compounds of formula (I) may be administered in single or divided doses by the oral, parenteral or topical routes. A suitable oral dosage for a compound of formula (I) would be in the range of about 0.5 mg to about 3 g per day. A preferred oral dosage for a compound of formula (I) would be in the range of about 100 mg to about 800 mg per day for a patient weighing 70 kg. In parenteral formulations, a suitable dosage unit may contain from about 0.1 to about 250 mg of said compounds, preferably about 1 mg to about 200 mg, whereas for topical administration, formulations containing about 0.01 to about 1% active ingredient are preferred. It should be understood, however, that the dosage administration from patient to patient would vary. The dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials include but are not limited to water, gelatin, talc, starch, magnesium stearate, gum arabic, vegetable oils, polyalkylene-glycols, petroleum jelly and the like.

The compounds of formula (I) can be used in combination with one or more other antiretroviral drug known to one skilled in the art, as a combined preparation useful for simultaneous, separate or sequential administration for treating HIV infection in an individual. Examples of antiretroviral drugs, including approved and investigational drugs, that may be used in combination therapy with compounds of formula (I) include but are not limited to:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, capravirine, etravirine, rilpivirine, GW695634 and BILR 355);

protease inhibitors (including but not limited to ritonavir, tipranavir, saquinavir, nelfinavir, indinavir, amprenavir, fosamprenavir, atazanavir, lopinavir, VX-385 and TMC-114);

entry inhibitors including but not limited to CCR5 antagonists (including but not limited to maraviroc (UK-427, 857), SCH-417690, GW873140 and TAK-652), CXCR4 antagonists (including but not limited to AMD-11070), fusion inhibitors (including but not limited to enfuvirtide (T-20)) and others (including but not limited to PRO-542 and BMS-488043);

integrase inhibitors (including but not limited to c-1605, BMS-538158 and JTK-303);

TAT inhibitors;

maturation inhibitors (including but not limited to PA-457);

immunomodulating agents (including but not limited to levamisole); and antifungal or antibacterial agents (including but not limited to fluconazole).

Moreover, a compound of formula (I) can be used with at least one other compound of formula (I).

The pharmaceutical preparations can be prepared in a conventional manner and finished dosage forms can be solid dosage forms, including but not limited to tablets, dragees, capsules, and the like, or liquid dosage forms, including but not limited to solutions, suspensions, emulsions and the like. The pharmaceutical preparations may be subjected to conventional pharmaceutical operations such as sterilization. Further, the pharmaceutical preparations may contain conventional adjuvants including but not limited to preservatives, stabilizers, emulsifiers, flavor-improvers, wetting agents, buffers, salts for varying the osmotic pressure and the like. Solid carrier material which can be used includes but is not limited to starch, lactose, mannitol, methyl cellulose, microcrystalline cellulose, talc, silica, dibasic calcium phosphate, and high molecular weight polymers (such as polyethylene glycol).

For parenteral use, a compound of formula (I) can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include but are not limited to, tartrate, citrate and acetate buffers, ethanol, propylene glycol, polyethylene glycol, complex formers (including but not limited to EDTA), antioxidants (including but not limited to sodium bisulfite, sodium metabisulfite, and ascorbic acid), high molecular weight polymers (including but not limited to liquid polyethylene oxides) for viscosity regulation and polyethylene derivatives of sorbitol anhydrides. Preservatives may also be added if necessary, including but not limited to benzoic acid, methyl or propyl paraben, benzalkonium chloride and other quaternary ammonium compounds.

The compounds of this invention may also be administered as a solution for nasal application and may contain in addition to the compounds of this invention suitable buffers, tonicity adjusters, microbial preservatives, antioxidants and viscosity-increasing agents in an aqueous vehicle. Examples of agents used to increase viscosity include but are not limited to polyvinyl alcohol, cellulose derivatives, polyvinylpyrrolidone, polysorbates or glycerin. Microbial preservatives added include but are not limited to benzalkonium chloride, thimerosal, chloro-butanol or phenylethyl alcohol.

Additionally, the compounds provided by the invention may be administrable by suppository.

Methodology and Synthesis

In general, the compounds of formula (I) are prepared by known methods from readily available starting materials, using reaction conditions known to be suitable for the reactants. Scheme 1 illustrates the general methods used to prepare the compounds of formula (I), wherein X is halo (e.g. Br or I), P is a protecting group, and $R^1$, $R^2$, $R^3$, $R^4$, $R^5$ and $R^6$ are as defined herein.

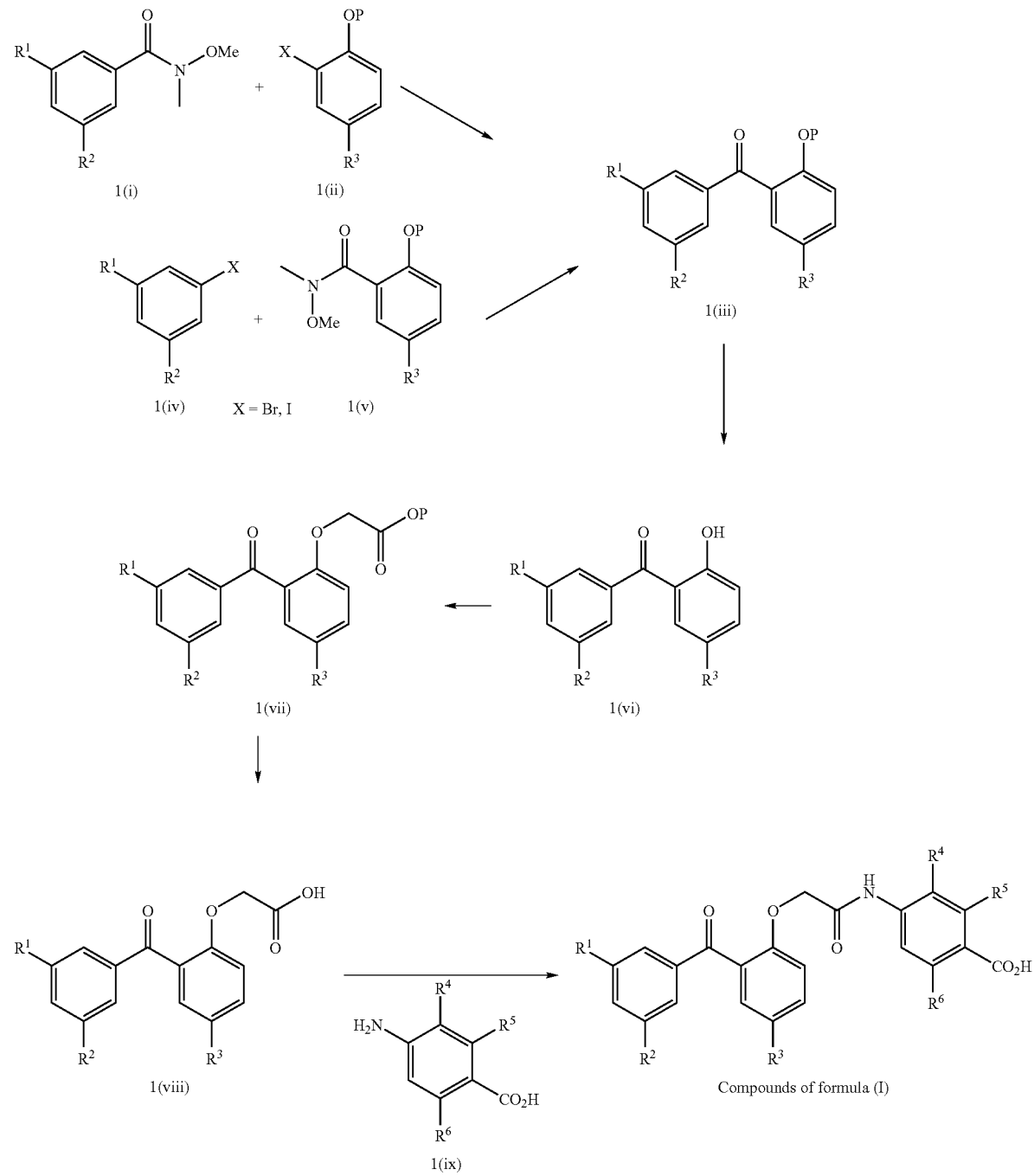

Scheme 1: General method for the synthesis of compound of formula (I)

Briefly, the aryllithium obtained by halogen-lithium exchange from 1(ii) can be acylated with amide 1(i) to give protected benzophenone 1(iii). Other organometallic derivatives can also be used to acylate amide 1(i). Alternatively, protected benzophenone 1(iii) can also be obtained from the aryllithium derived from 1(iv) upon acylation with amide 1(v). $R^1$ and $R^2$ substituents (e.g. Br) of intermediate 1(iii) can also be converted to other $R^1$ and $R^2$ substituents (e.g. CN, cPr) using methods known to one skilled in the art. Protected benzophenone 1(iii) is deprotected to give the hydroxybenzophenone 1(vi) by methods known to those skilled in the art. For example, the methyl ether of benzophenone 1(iii) (P=$CH_3$) may be demethylated conveniently by treatment with $BBr_3$. The hydroxybenzophenone 1(vi) can be O-alkylated with an α-haloacetic acid ester in the presence of base to yield the corresponding ether 1(vii)(P=—$CH_3$, —$CH_2CH_3$ or —$C(CH_3)_3$, for example). Cleavage of the ester protecting group using well-known conditions, such as aqueous base (in the case where P=—$CH_3$, or —$CH_2CH_3$) or trifluoroacetic acid (in the case where P=—$C(CH_3)_3$) gives acid 1(viii). Alternatively, hydroxybenzophenone 1(vi) may be transformed directly into acid 1(viii) by alkylation with an α-haloacetic acid. This approach for the preparation of benzophenone 1(viii) has been described by J. H. Chan et al. (J. Med. Chem. 2004, 47, 1175-1182). Finally, the coupling of acid 1(viii) with aminobenzoic acid derivative 1(ix) using appropriate activation of the acid (for example, transformation to the corresponding intermediate acyl chloride) can provide compounds of formula (I).

Scheme 2 illustrates a general method used to prepare non-commercially available 4-aminobenzoic acids 1(ix), wherein P is a protecting group, $R^4$ is methyl or chloro and $R^5$ and $R^6$ are as defined herein.

Scheme 2: General method for the synthesis of 4-aminobenzoic acid intermediates

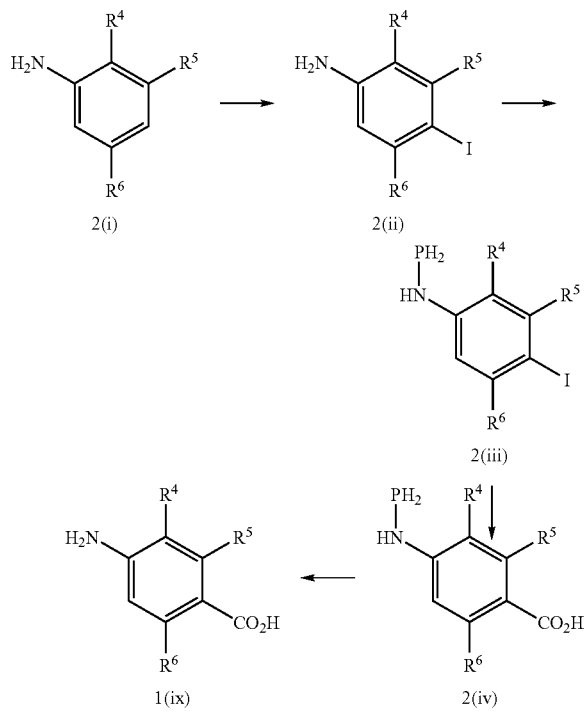

Briefly, aniline 2(i) can be transformed to iodo derivative 2(ii). Protection of the aniline by methods known to those of skill in the art (such as, for example, transformation to the corresponding acetamide wherein P=—C(=O)$CH_3$) gives 2(iii). The aryllithium or arylmagnesium halide obtained by iodine-metal exchange from 2(iii) can be transformed to 2(iv) by trapping with carbon dioxide. Alternative methods to transform 2(iii) to acid 2(iv) are known to the skilled in the art. Finally, removal of the protective group by well known methods such as treatment with aqueous base gives 4-aminobenzoic acid 1(ix). Scheme 3 illustrates an alternative method used to prepare non-commercially available 4-aminobenzoic acids 1(ix), wherein P is a protecting group such as —$CH_3$ or —$CH_2CH_3$, $R^4$ is chloro or bromo, $R^5$ is as defined herein and $R^6$ is H.

Scheme 3: Alternative method for the synthesis of 4-aminobenzoic acid intermediates

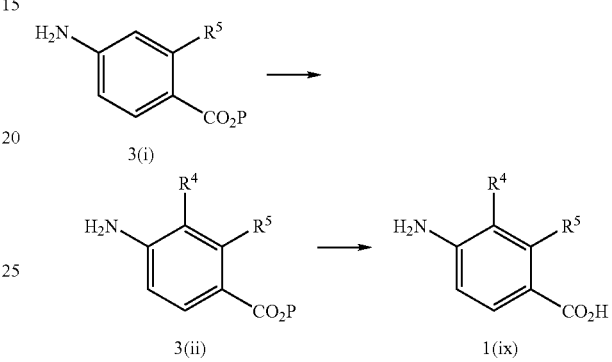

Briefly, aniline 3(i) can be transformed to 3(ii)($R^4$=Cl or Br) by chlorination or bromination. Removal of the protecting group by well known methods such as treatment with aqueous base gives 4-aminobenzoic acid 1(ix).

EXAMPLES

The present invention is illustrated in further detail by the following non-limiting examples. All reactions were performed in a nitrogen or argon atmosphere unless otherwise stated. Room temperature is from about 18° C. to about 22° C. (degrees Celsius). Solution percentages or ratios express a volume to volume relationship, unless stated otherwise. Purification by reverse phase HPLC (RP-HPLC) was performed using a gradient of MeCN/$H_2O$ containing TFA (0.06%) (CombiPrep ODS-AQ 50×20 mm, 5μ, 120 A). Analytical HPLC was carried out under standard conditions using a Combiscreen ODS-AQ C18 reverse phase column, YMC, 50×4.6 mm i.d., 5 μM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
Bu: butyl;
tBu: 1,1-dimethylethyl(tert-butyl);
cPr: cyclopropyl;

Chaps: 3-{(3-cholamidopropyl)dimethylammonio}-1-propanesulfonate;
dGTP: deoxyguanosine triphosphate;
DMF: N,N-dimethylformamide;
DMSO: dimethylsulfoxide;
DTT: DL-dithiothreitol;
EDTA: ethylenediaminetetraacetic acid;
Et: ethyl;
$Et_3N$: triethylamine;
$Et_2O$: diethyl ether;
EtOH: ethanol;
EtOAc: ethyl acetate;
GSH: glutathione;
HPLC: high performance liquid chromatography;
iPr: 1-methylethyl(isopropyl);
Me: methyl;
MeOH: methanol;
MeCN: acetonitrile;
n-BuLi: n-butyllithium;
NMR: nuclear magnetic resonance;
Ph: phenyl;
Pr: propyl;
RP-HPLC: reverse phase high performance liquid chromatography;
TFA: trifluoroacetic acid;
THF: tetrahydrofuran;
TLC: thin layer chromatography;
Tris: tris(hydroxymethyl)aminomethane.

Syntheses

The following examples illustrate methods for preparing compounds of the invention.

Example 1

Benzophenone Intermediate 1.6

The modified method of J. H. Chan et al. (J. Med. Chem. 2004, 47, 1175-1182) was followed.

a) Compound 1.2

Acyl chloride 1.1 (5.00 g, 21.0 mmol) was added dropwise to an ice-cold solution of MeNH(OMe).HCl (2.80 g, 28.1 mmol) and $Et_3N$ (9.00 mL, 63.9 mmol) in $CHCl_3$ (50 mL). The reaction mixture was stirred at 0° C. for 45 min and at room temperature for 3 h then was concentrated under reduced pressure. The residue was partitioned between water and EtOAc. The organic layer was washed with water and brine, dried ($MgSO_4$), filtered and concentrated under reduced pressure to give compound 1.2 (4.78 g, 91% yield) as a brown oil.

b) Compound 1.4

A solution of 2.5 M n-BuLi in hexane (28.7 mL, 71.7 mmol) was added dropwise to a solution of compound 1.3 (16.0 g, 71.7 mmol) in $Et_2O$ (300 mL) at −78° C. The reaction mixture was stirred at −78° C. for 20 min, then a solution of compound 1.2 (18.0 g, 71.7 mmol) in $Et_2O$ (10 mL) was added dropwise. The reaction mixture was stirred at −78° C. for 30 min then was allowed to warm to room temperature and stirred at room temperature for 30 min. The dark mixture was poured into water and the mixture was extracted with EtOAc (2×). The organic layers were washed with water and brine, dried ($MgSO_4$), filtered and concentrated under reduced pressure. The residue was triturated with hexane to give 1.4 (13.3 g, 56% yield) as a white solid.

c) Compound 1.5

To a cold (−78° C.) solution of compound 1.4 (5.95 g, 17.9 mmol) in $CH_2Cl_2$ (100 mL) was added a solution of 1.0 M $BBr_3$ in $CH_2Cl_2$ (50.0 mL, 50.0 mmol). The reaction mixture was stirred at −78° C. for 1 h then was allowed to warm to room temperature and stirred at this temperature for 4 h. The mixture was poured into ice-water and extracted with $CH_2Cl_2$

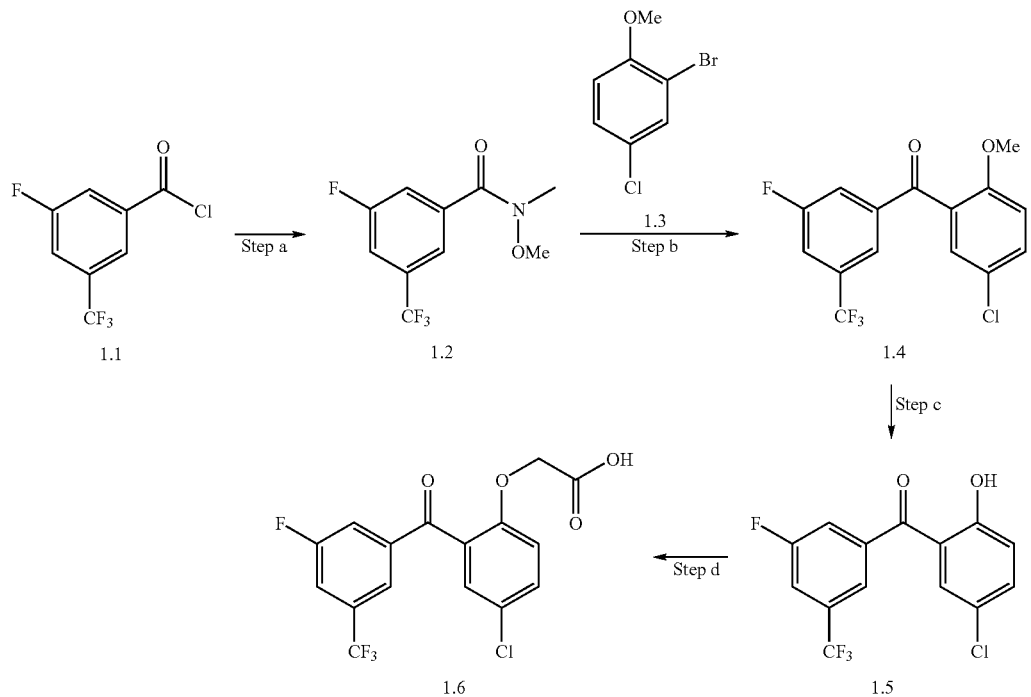

(3×). The combined organic layers were washed with water and brine, dried (MgSO$_4$), filtered, and concentrated under reduced pressure to give compound 1.5 (5.78 g, 100% yield) as a brown solid.

d) Compound 1.6

To a solution of phenol 1.5 (5.75 g, 18.0 mmol) in acetone (40 mL) were added K$_2$CO$_3$ (10.0 g, 72.3 mmol) and ethyl bromoacetate (2.20 mL, 19.4 mmol), and the mixture was heated at reflux for 1 h. Upon cooling the reaction mixture was concentrated, diluted with EtOAc and the resulting solution was successively washed with water and brine, dried (MgSO$_4$), filtered and concentrated under reduced pressure. The residue was dissolved in a mixture of THF (60 mL), EtOH (20 mL) and water (20 mL) and LiOH.H$_2$O (1.30 g, 31.0 mmol) was added. The solution was stirred at room temperature for 3 days then was slowly acidified with aqueous 1 N HCl solution. The mixture was concentrated under reduced pressure to a volume of 30 mL and was partitioned between water and EtOAc. The aqueous layer was extracted with EtOAc. The combined organic layers were washed with water and brine, dried (MgSO$_4$), filtered and concentrated under reduced pressure. The residue was allowed to crystallize from a mixture of Et$_2$O and hexane to give compound 1.6 (5.02 g, 75% yield) as a beige solid.

Example 2

Benzophenone Intermediate 2.7 tion and brine, dried (MgSO$_4$), filtered and concentrated under reduced pressure to give compound 2.2 (24.3 g, 97% yield) as a white solid.

b) Compound 2.4

Using a method similar to the one described in Example 1, Step b, but starting with compound 2.3 (4.40 g, 17.3 mmol) and compound. 2.2 (3.98 g, 17.3 mmol), compound 2.4 (3.60 g, 60% yield) was obtained as a yellow solid.

c) Compound 2.5

A mixture of compound 2.4 (8.63 g, 25.1 mmol) and CuCN (6.75 g, 75.4 mmol, dried at 100° C. under reduced pressure for 18 h) in DMF (50 mL) was heated at 185° C. for 3.5 h. The cooled reaction mixture was diluted with EtOAc and the resulting solution was washed with concentrated NH$_4$OH solution, water and brine, dried (MgSO$_4$), filtered and concentrated to a volume of about 50 mL. Hexane (150 mL) was then added and the resulting precipitate was recovered by filtration and dried to give compound 2.5 (5.70 g, 78% yield) as a off-white solid.

d) Compound 2.6

A solution of 1.0 M BBr$_3$ in CH$_2$Cl$_2$ (50.0 mL, 50.0 mmol) was added over 15 min to a cold (−78° C.) solution of compound 2.5 (5.70 g, 19.7 mmol) in CH$_2$Cl$_2$ (120 mL). The reaction mixture was stirred at −78° C. for 1 h then was allowed to warm to room temperature (30 min). The mixture was poured into ice-water. The phases were separated. The aqueous layer was extracted with CH$_2$Cl$_2$ (3×). The combined

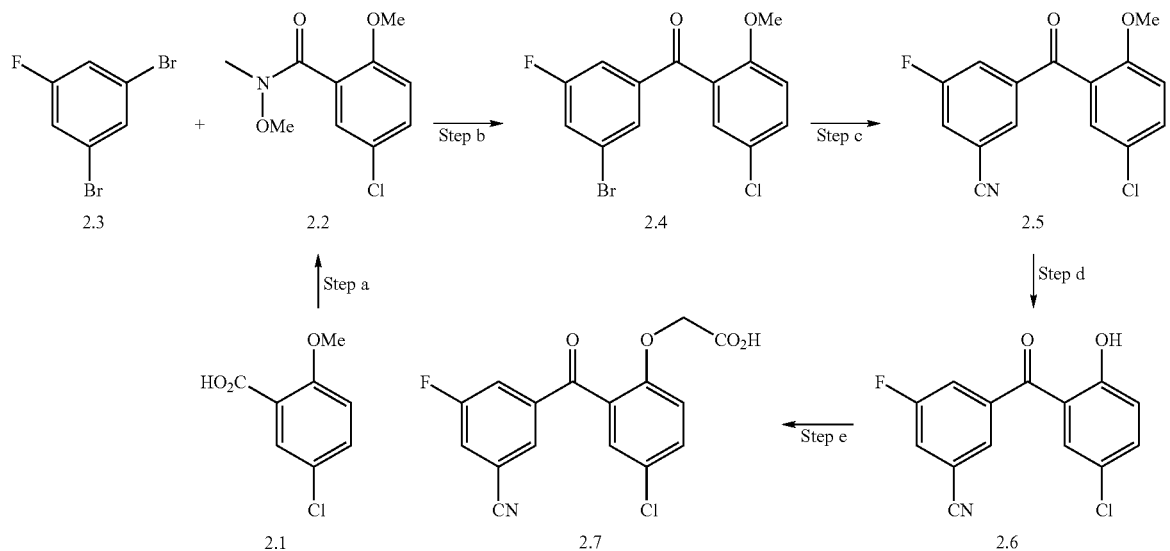

a) Compound 2.2

To a solution of acid 2.1 (20.3 g, 109 mmol) in CH$_2$Cl$_2$ (500 mL) were added (COCl)$_2$ (14.0 mL, 157 mmol) and DMF (0.2 mL). After 2 h the reaction mixture was concentrated under reduced pressure. A solution of the resulting acyl chloride (22.3 g, 109 mmol) in CH$_2$Cl$_2$ (80 mL) was added dropwise to a solution of Et$_3$N (45.0 mL, 323 mmol) and MeNH(OMe).HCl (13.9 g, 142 mmol) in CH$_2$Cl$_2$ (300 mL). The resulting solution was stirred for 2 h at room temperature. The reaction mixture diluted with EtOAc was successively washed with aqueous 1 N HCl solution, aqueous saturated NaHCO$_3$ soluorganic layers were washed with water, dried (MgSO$_4$), filtered and concentrated under reduced pressure. The residue was dissolved in EtOAc (30 mL) and hexane (100 mL) was added. The resulting green solid obtained by filtration was washed with hexane (10 mL), dried under reduced pressure to give compound 2.6 (4.72 g, 87% yield).

e) Compound 2.7

A solution of phenol 2.6 (4.72 g, 17.1 mmol). K$_2$CO$_3$ (7.09 g, 51.4 mmol) and t-butyl bromoacetate (2.82 mL, 17.5 mmol) in acetone (75 mL) was heated at 50° C. for 1.5 h. The cooled reaction mixture diluted with EtOAc was washed with water (2×) and brine, dried (MgSO$_4$), filtered and concentrated under reduced pressure. A solution of the residue in TFA (25 mL) and CH$_2$Cl$_2$ (50 mL) was stirred at room temperature for 1 h. The reaction mixture was concentrated under reduced pressure to a volume of 40 mL, hexane (100 mL) was added and the resulting suspension was filtered. The solid was washed with hexane and dried under reduced pressure to give compound 2.7 (5.14 g, 90% yield) as a white solid.

Example 3

Benzophenone Intermediate 3.2

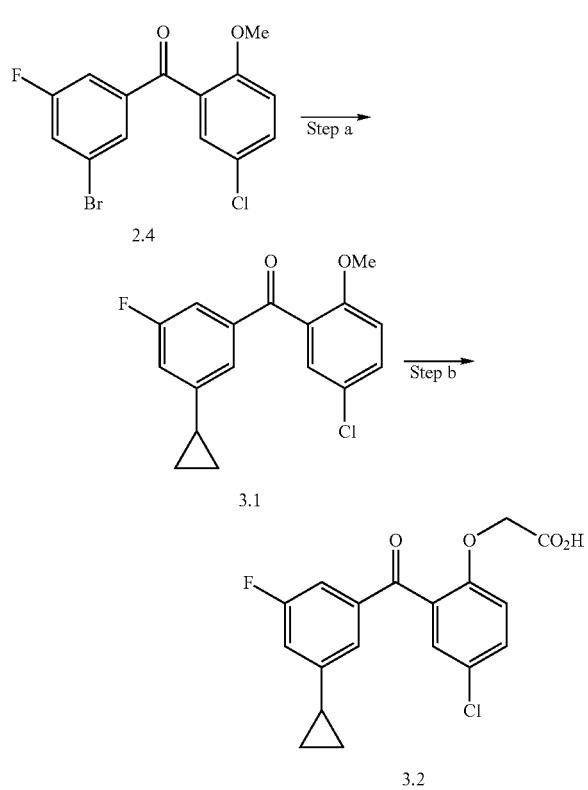

b) Compound 3.2

Using a method similar to the one described in Example 1, Steps c and d, but starting with compound 3.1 (1.20 g, 3.94 mmol), acid 3.2 (1.30 g, 95% yield) was obtained as a white solid.

Example 4

Benzophenone Intermediate 4.1

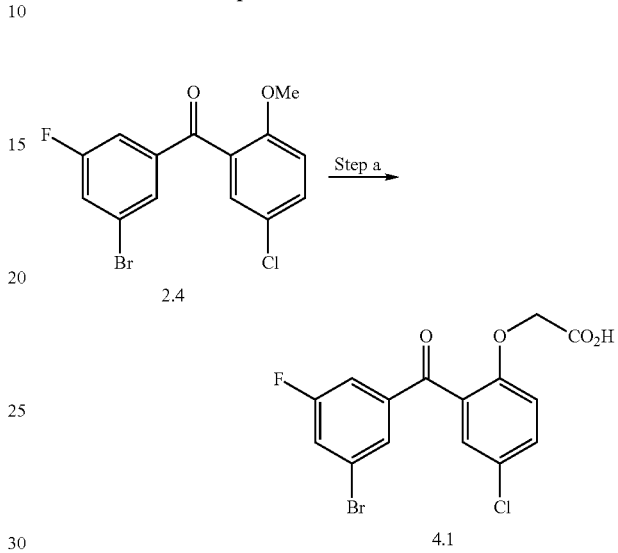

a) Compound 4.1

Using a method similar to the one described in Example 1, Steps c and d, but starting with compound 2.4 (2.00 g, 5.82 mmol), compound 4.1 (1.16 g, 51% yield) was obtained as a beige solid.

Using the methods of Example 1 or Example 2, but starting with commercially available appropriately substituted benzoic acid or benzoyl chloride and bromobenzene intermediates, other benzophenone intermediates used in the preparation of compounds of formula (I) were prepared.

Example 5

Aniline Intermediate 5.5

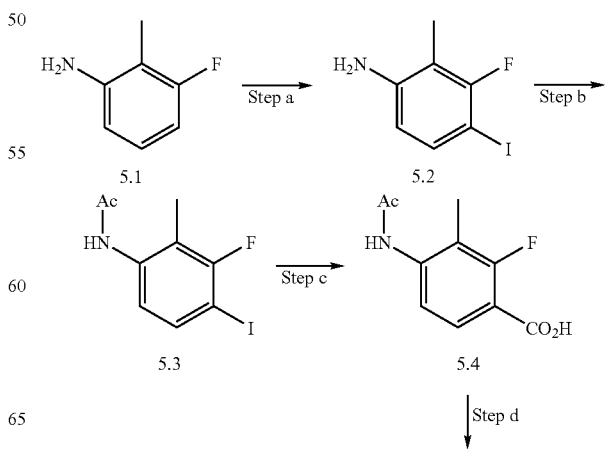

a) Compound 3.1

A solution of 1.6 M n-BuLi in hexane (7.2 mL, 11.5 mmol) was added over 45 min to a cold (−78° C.) solution of cyclopropylbromide (1.17 mL, 14.5 mmol) in THF (40 mL). After 1 h, a solution of ZnBr$_2$ (flame dried under high vacuum, 2.88 g, 12.8 mmol) in THF (10 mL) was added by cannula and the mixture was allowed to warm to room temperature. After 1 h a solution of compound 2.4 (from Example 2)(2.00 g, 5.82 mmol) in THF (30 mL) and Pd(PPh$_3$)$_4$ (672 mg, 0.58 mmol, under stream of nitrogen) were added. The reaction mixture was then heated at reflux for 16 h, cooled in an ice bath and quenched with aqueous saturated NaHCO$_3$ solution. The resulting mixture was extracted with EtOAc several times and the combined organic layers were successively washed with water and brine, dried (MgSO$_4$), filtered and concentrated under reduced pressure. The crude product was purified by flash chromatography (hexane/EtOAc, 90/10) to give compound 3.1 (1.25 g, 70% yield) as a pale yellow solid.

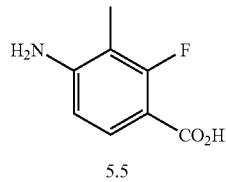

5.5 a) Compound 5.2

To a solution of aniline 5.1 (5.20 g, 41.6 mmol) in acetic acid (30 mL) was added KI (8.46 g, 51 mmol), $NaBO_3 \cdot 4H_2O$ (7.28 g, 47 mmol) and $(NH_4)_2MoO_4$ (7.9 g, 40 mmol). After 30 min the reaction was poured into a mixture of aqueous saturated $NaHCO_3$ solution (50 mL) and aqueous 10% $Na_2S_2O_3$ solution (10 mL). The aqueous layer was extracted with $Et_2O$ and the combined organic phases were washed with brine, dried ($MgSO_4$) filtered and concentrated under reduced pressure to give compound 5.2 (9.96 g, 95% yield) as a beige solid.

b) Compound 5.3

To a solution of aniline 5.2 (2.20 g, 8.76 mmol) in THF (25 mL) were added $Et_3N$ (1.40 mL, 10 mmol) and acetyl chloride (0.64 mL, 9.0 mmol). After 3 h the reaction mixture was diluted with $Et_2O$ and the resulting solution washed with aqueous 1 N HCl solution, water and brine, dried ($MgSO_4$) filtered and concentrated under reduced pressure to give compound 5.3 (2.40 g, 93% yield) as a beige solid.

c) Compound 5.4

To a solution of 5.3 (0.30 g, 1.02 mmol) in THF (10 mL) was added NaH (44.0 mg, 1.10 mmol). After 30 min the reaction was cooled to −30° C. and 2.0 M i-PrMgCl solution in THF (0.60 mL, 1.2 mmol) was added. The reaction mixture was allowed to warm to room temperature and $CO_2(g)$ was bubbled through the solution for 15 min. Upon quenching with aqueous 1 N HCl solution (5 mL), the reaction mixture was extracted with EtOAc. The combined organic phases were washed with brine, dried ($MgSO_4$), filtered and concentrated under reduced pressure. The resulting solid was triturated with $Et_2O$ to give compound 5.4 (60 mg, 28% yield) as a beige solid.

d) Compound 5.5

A solution of compound 5.4 (40 mg, 0.19 mmol) in aqueous 5 N NaOH solution (3 mL) was heated at 80° C. for 3 h. Upon cooling the reaction mixture was acidified with aqueous 12 N HCl solution and extracted with EtOAc. The combined organic phase were washed with brine, dried ($MgSO_4$), filtered and concentrated under reduced pressure to give compound 5.5 (25 mg, 78% yield) as a white solid.

Example 6

Aniline Intermediate 6.4

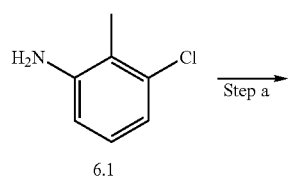

6.1

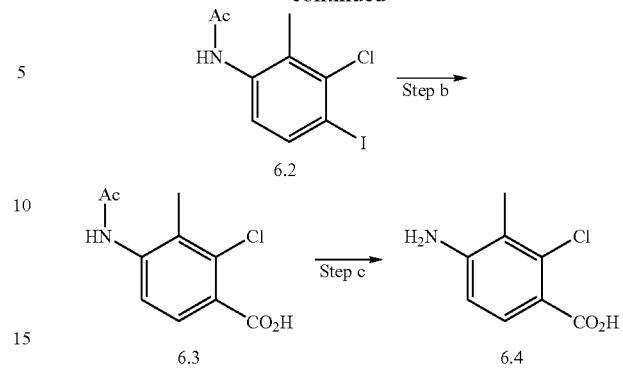

a) Compound 6.2

Following a procedure similar to the one described in Example 5 steps a and b but starting with compound 6.1 (1.98 g, 14.0 mmol), compound 6.2 (2.70 g, 62% yield) was obtained as a grey solid.

b) Compound 6.3

Following a procedure similar to the one described in Example 5 step c but starting with compound 6.2 (1.00 g, 3.23 mmol), compound 6.3 (300 mg, 41% yield) was obtained as a white solid.

c) Compound 6.4

Following a procedure similar to the one described in Example 5 step d but starting with compound 6.3 (200 mg, 0.88 mmol), compound 6.4 (150 mg, 92% yield) was obtained as a white solid.

Example 7

Aniline Intermediate 7.4

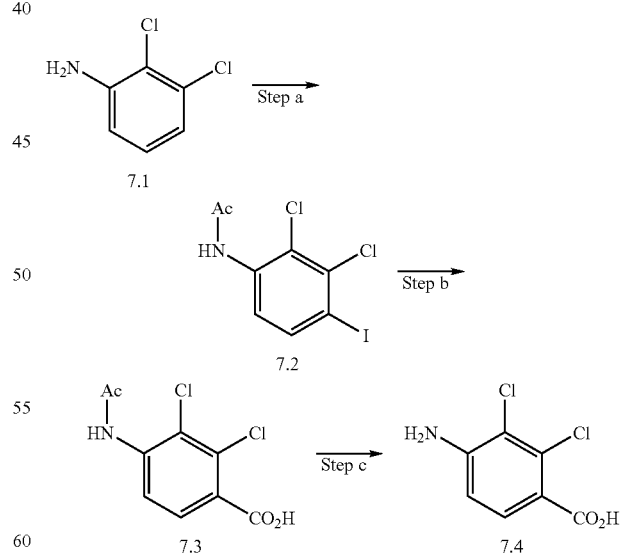

a) Compound 7.2

Following a procedure similar to the one described in Example 5 steps a and b but starting with compound 7.1 (2.27 g, 14.0 mmol), compound 7.2 (2.80 g, 61% yield) was obtained as a light pink solid.

b) Compound 7.3

Following a procedure similar to the one described in Example 5 step c but starting with compound 7.2 (1.00 g, 3.03 mmol), compound 7.3 (420 mg, 56% yield) was obtained as a white solid.

c) Compound 7.4

Following a procedure similar to the one described in Example 5 step d but starting with compound 7.3 (250 mg, 1.01 mmol), compound 7.4 (180 mg, 87% yield) was obtained as a light pink solid.

Example 8

Aniline Intermediate 8.3

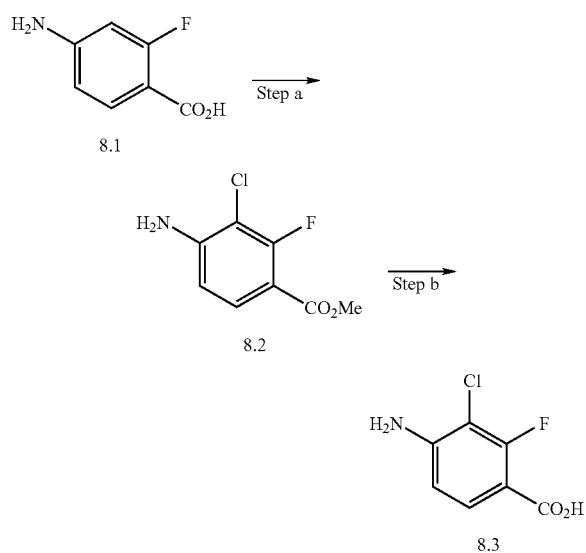

a) Compound 8.2

To a solution of aniline 8.1 (1.00 g, 6.45 mmol) in MeCN (10 mL) was added N-chlorosuccinimide (860 mg, 6.45 mmol). The reaction mixture was heated at 60° C. for 3 h. After cooling to room temperature the reaction mixture was concentrated under reduced pressure. The residue was dissolved in $CH_2Cl_2$, treated with an ethereal solution of diazomethane (~0.6 M, 20 mL) and concentrated under reduced pressure. The residue was purified by flash chromatography (hexane/EtOAc, 90/10 to 60/40) to give compound 8.2 (280 mg, 21% yield) as a white solid.

b) Compound 8.3

To a solution of aniline 8.2 (29.5 mg, 145 µmol) in THF (5 mL) and MeOH (4 mL) was added an aqueous 1 N NaOH solution (4 mL). After 16 h aqueous 1 N HCl (25 mL) was added and the mixture was extracted several times with EtOAc. The combined organic layers were successively washed with water and brine, dried ($MgSO_4$), filtered and concentrated under reduced pressure to give compound 8.3 (25.4 mg, 92% yield) as a beige solid.

Example 9

Entry 1003

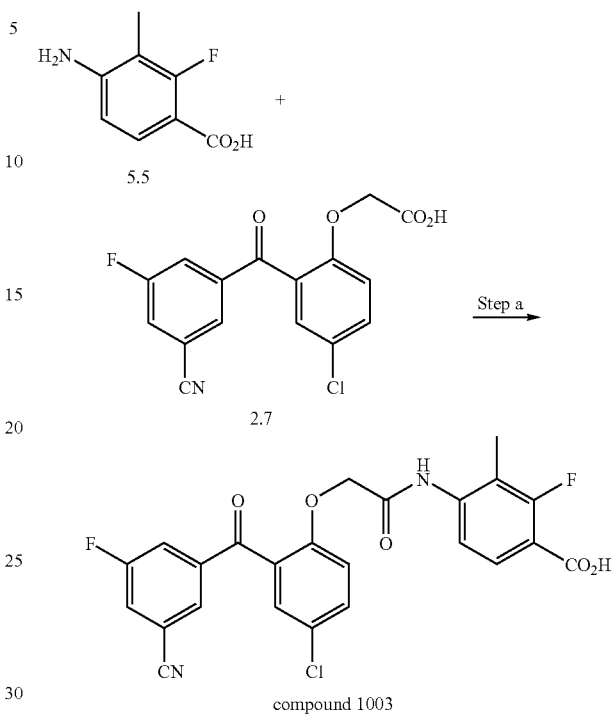

compound 1003 a) Compound 1003

To a solution of acid 2.7 (from Example 2)(39 mg, 0.12 mmol) in $CH_2Cl_2$ (2 mL) were added oxalyl chloride (11 µL, 0.13 mmol) and DMF (1 drop). After 2 h the reaction was concentrated under reduced pressure to give the corresponding acyl chloride. Pyridine (12 µL, 0.15 mmol) and compound 5.5 (from Example 5)(20 mg, 0.12 mmol) were added to a solution of the crude acyl chloride in THF (2 mL) at room temperature and the resulting solution was stirred for 2 h. The reaction mixture was concentrated under reduced pressure and the crude acid was purified by RP-HPLC. The pure fractions were combined and concentrated to give compound 1003 (10 mg, 17% yield) as a white solid.

$^1$H-NMR (DMSO-$d_6$): δ 13.06 (broad s, 1H), 9.57 (s, 1H), 8.16 (m, 1H), 8.05 (s, 1H), 7.94 (m, 1H), 7.69 (dd, J=9.0, 2.7 Hz, 1H), 7.66 (m, 1H), 7.56 (d, J=2.7 Hz, 1H), 7.45 (m, 1H), 7.24 (d, J=9.0 Hz, 1H), 4.82 (s, 2H), 2.04 (s, 3H).

Example 10

Entry 1001

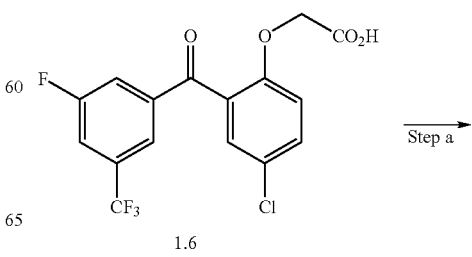

23

-continued

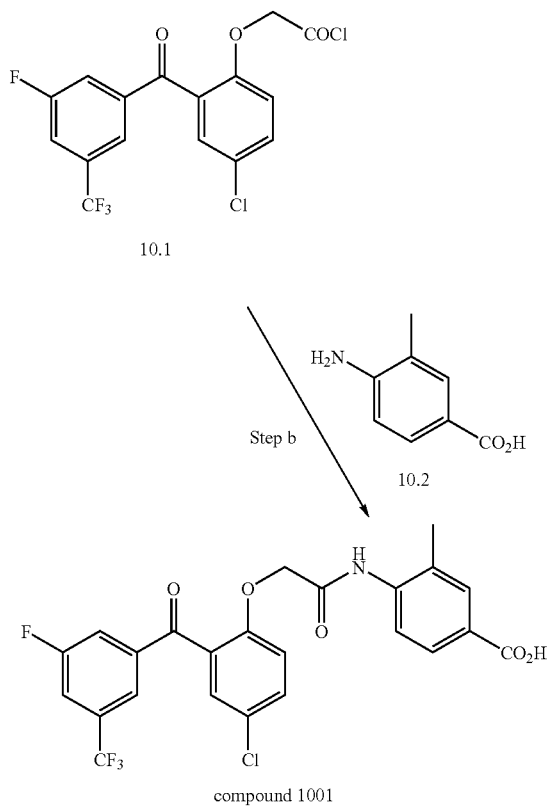

10.1 compound 1001

Example 11

Entry 1002

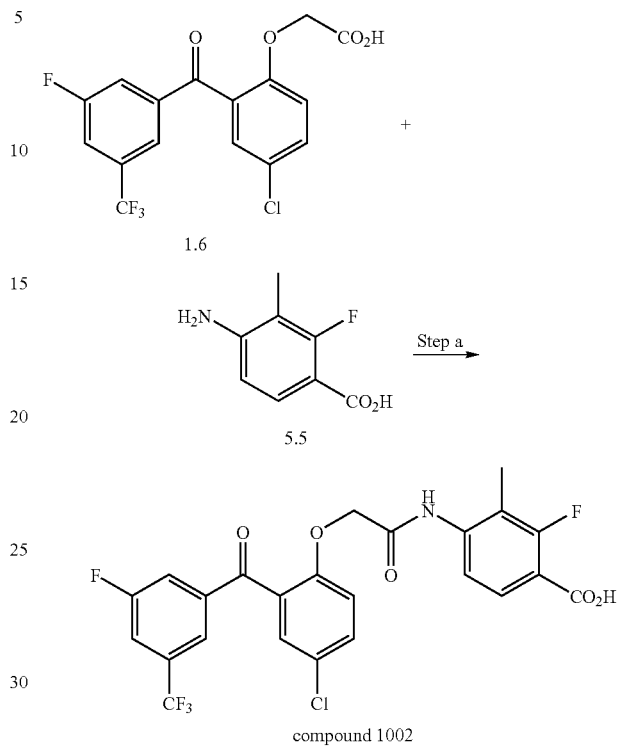

compound 1002 a) Compound 10.1

To a solution of acid 1.6 (from Example 1)(150 mg, 0.398 mmol) in CH$_2$Cl$_2$ (10 mL) at room temperature were added oxalyl chloride (104 µL, 1.19 mmol) and DMF (1 drop). The reaction mixture was stirred for 30 min then was concentrated under reduced pressure to give acyl chloride 4.1 (157 mg, 100% yield).

b) Compound 1001

Commercially available aniline 10.2 (120 mg, 0.796 mmol) and pyridine (161 mL, 1.99 mmol) were successively added to a solution of crude acyl chloride 10.1 (157 mg, 0.398 mmol) in THF (10 mL) at room temperature. The reaction mixture was stirred at room temperature for 1 h then was diluted with EtOAc. The resulting solution was successively washed with aqueous 0.5 N HCl solution (2×), water, aqueous saturated NaHCO$_3$ solution and brine, dried (MgSO$_4$), filtered and concentrated under reduced pressure. Half the crude residue was purified by RP-HPLC. The pure fractions were combined and concentrated to give compound 1001 (44 mg, 43% yield) as a white solid. $^1$H-NMR (DMSO-d$_6$): δ 12.81 (broad s, 1H), 9.35 (s, 1H), 8.01 (d, J=8.4 Hz, 1H), 7.89 (s, 1H), 7.88 (d, J=7.9 Hz, 1H), 7.77 (s, 1H), 7.72 (dd, J=8.4, 1.4 Hz, 1H), 7.67 (dd, J=8.8, 2.5 Hz, 1H), 7.61 (d, J=8.4 Hz, 1H), 7.55 (d, J=2.8 Hz, 1H), 7.23 (d, J=9.0 Hz, 1H), 4.81 (s, 2H), 2.15 (s, 3H).

a) Compound 1002

Following a procedure similar to the one described in Example 10, steps a and b but starting with acid 1.6 (from Example 1)(71.0 mg, 188 mmol) and aniline 5.5 (from Example 5)(32.5 mg, 188 mmol), compound 1002 (49.0 mg, 49% yield) was obtained as a white solid. $^1$H-NMR (DMSO-d$_6$): δ 13.05 (s, 1H), 9.54 (s, 1H), 8.01 (d, J=8.4 Hz, 1H), 7.87 (m, 2H), 7.65 (m, 2H), 7.55 (d, J=2.8 Hz, 1H), 7.40 (d, J=9 Hz, 1H), 7.23 (d, J=9 Hz, 1H), 4.81 (s, 2H), 2.01 (s, 3H).

Example 12

Entry 1004

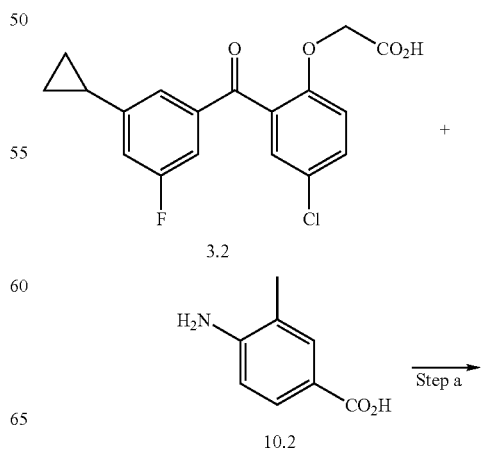

-continued

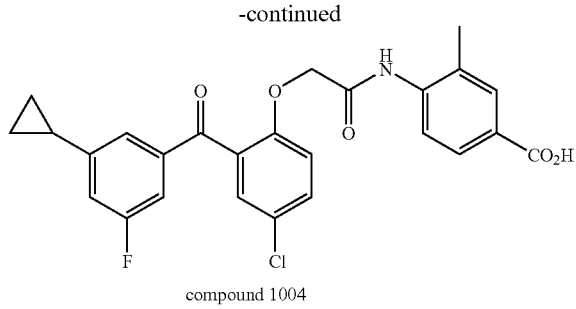

compound 1004 a) Compound 1004

Following a procedure similar to the one described in Example 5, step e but starting with compound 3.2 (from Example 3)(60.0 mg, 172 mmol) and compound 10.2 (from Example 10)(26.5 mg, 346 mmol), compound 1004 (13.3 mg, 16% yield) was obtained as a white solid. $^1$H-NMR (DMSO-$d_6$): δ 12.19 (s, 1H), 9.19 (s, 1H), 7.77 (s, 1H), 7.74-7.61 (m, 3H), 7.45 (d, J=2.5 Hz, 1H), 7.38 (s, 1H), 7.27 (d, J=9.2 Hz, 1H), 7.22 (d, J=9.0 Hz, 1H), 7.15 (d, J=10 Hz, 1H), 4.81 (s, 2H), 2.15 (s, 3H), 2.04-1.99 (m, 1H), 0.98-0.93 (m, 2H), 0.71-0.67 (m, 2H).

Example 13

Reverse Transcriptase (RT) Assays

Enzymatic Assay ($IC_{50}$)

The enzymatic assay employed is described as follows: The reverse transcriptase (RT) enzyme assay has been adapted to a 96-well microtiter plate format and uses PicoGreen™ as a fluorescent intercalator. More explicitly, the HIV-1 RT enzyme was thawed and appropriately diluted into Tris/HCl 50 mM pH 7.8 containing NaCl 60 mM, $MgCl_2 \cdot 6H_2O$ 2 mM, DTT 6 mM, GSH 2 mM and 0.02% w/v Chaps to give ≈10 nM enzyme. To 10 μL of this enzyme solution was added 10 μL of inhibitor solution (40 μM to 2.032 nM inhibitor in the same assay buffer as above containing 4% v/v DMSO). The plate was pre-incubated for 15 minutes at room temperature before proceeding to the next step. In this pre-incubation step, the highest and lowest inhibitor concentrations were 20 μM and 1.016 nM respectively and the concentration of DMSO was 2% v/v. Then the enzymatic reaction was initiated by addition of 20 μL of substrate solution. The final reaction mixture contained Tris/HCl 50 mM pH 7.8, NaCl 60 mM, $MgCl_2 \cdot 6H_2O$ 2 mM, DTT 6 mM, GSH 2 mM, CHAPS 0.02% w/v, DMSO 1% v/v, poly rC 45 nM, $dG_{15}$ 4.5 nM, dGTP 3.6 μM, and ≈2.5 nM enzyme. In this incubation step, the highest and lowest inhibitor concentrations were 10 μM and 0.508 nM respectively. After addition of the substrate cocktail, the plate was covered with a plastic seal and incubated for 50 minutes at 37° C. in a dry incubator. The reaction was then quenched by addition of 5 μL of EDTA 0.5 M. The plate was shaken for 30 seconds at medium speed and incubated for 5 minutes at room temperature. Then 160 μL of PicoGreen™ 1:400 dilution from commercial stock (diluted in Tris 20 mM pH 7.5 with EDTA 1 mM) was added and the plate was shaken for 30 seconds and incubated for 10 minutes at room temperature. The plate was then analyzed using a POLARstar Galaxy fluorometer (BMG Labtechnologies) with $\lambda_{ex}$ and $\lambda_{em}$ of 485 nm and 520 nm respectively. Each well was read for 1.25 second. Each row contained at its extremities a blank and a control well.

P24 Cellular Assay ($EC_{50}$)

The p24 assay is as described in WO 01/96338, pages 59-60, herein incorporated by reference.

C8166 HIV-1 Luciferase Assay ($EC_{50}$)

The luciferase assay is as described in WO 2004/050643, pages 73-75, herein incorporated by reference.

Table

Table 1 illustrates further compounds of the present invention, which can be synthesized in analogy to the methods as described hereinbefore, optionally modified by procedures known to the one skilled in the art. All compounds shown in the table are active in at least one of the assays described in Example 13; showing $IC_{50}$ and/or $EC_{50}$ values of less than 1 μM.

Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | $R^1$ | $R^2$ | $R^4$ | $R^5$ | $R^6$ | $t_R$ (min) | MS ($MH^+$) |
|---|---|---|---|---|---|---|---|
| 1001 | F | $CF_3$ | Me | H | H | 6.9 | 510.1 512.1 |
| 1002 | F | $CF_3$ | Me | F | H | 7.0 | 526.1 528.0 (M − H)$^-$ |
| 1003 | F | CN | Me | F | H | 6.3 | 485.2 487.2 |
| 1004 | F | cyclopropyl | Me | H | H | 7.1 | 482.2 484.2 |
| 1005 | F | Cl | Me | H | H | 7.0 | 474.1 476.1 478.1 (M − H)$^-$ |
| 1006 | H | CN | Me | H | H | 7.1 | 447.1 449.1 (M − H)$^-$ |
| 1007 | F | CN | Me | H | H | 6.3 | 465.1 467.1 (M − H)$^-$ |
| 1008 | F | $CF_3$ | Cl | H | H | 7.2 | 528.1 530.0 532.0 |

TABLE 1-continued

| Cpd | R¹ | R² | R⁴ | R⁵ | R⁶ | $t_R$ (min) | MS (MH⁺) |
|---|---|---|---|---|---|---|---|
| 1009 | F | CN | Cl | H | H | 6.4 | 485.1<br>487.1<br>489.0<br>(M − H)⁻ |
| 1010 | F | CF₃ | Cl | F | H | 7.2 | 546.1<br>548.1<br>550.0<br>(M − H)⁻ |
| 1011 | F | cyclopropyl | Me | F | H | 7.0 | 500.1<br>502.1 |
| 1012 | F | Br | Me | F | H | 6.9 | 536.0<br>538.0<br>540.0<br>(M − H)⁻ |
| 1013 | F | Cl | Me | F | H | 6.9 | 492.0<br>494.0<br>496.0<br>(M − H)⁻ |
| 1014 | F | Br | Me | H | H | 6.8 | 521.9<br>523.9 |
| 1015 | H | Br | Me | H | H | 5.9 | 500.0<br>502.0<br>504.0<br>(M − H)⁻ |
| 1016 | H | Br | Me | F | H | 6.7 | 521.8<br>523.9 |
| 1017 | H | CN | Me | F | H | 5.9 | 467.0<br>469.0 |
| 1018 | Cl | CN | Me | H | H | 6.4 | 481.1<br>483.1<br>484.0<br>(M − H)⁻ |
| 1019 | F | cyclopropyl | Br | H | H | 7.2 | 544.0<br>546.0<br>548.0<br>(M − H)⁻ |
| 1020 | F | CF₃ | Br | H | H | 7.1 | 572.0<br>573.9<br>576.0<br>(M − H)⁻ |
| 1021 | Cl | CN | Me | F | H | 6.4 | 523.1<br>525.0<br>(M + Na)⁺ |
| 1022 | F | CF₃ | Cl | Cl | H | 7.1 | 561.7<br>563.7<br>565.7<br>567.7<br>(M − H)⁻ |
| 1023 | F | CF₃ | Me | Me | H | 6.8 | 521.8<br>523.8<br>(M − H)⁻ |
| 1024 | F | CF₃ | Me | Cl | H | 6.9 | 543.8<br>545.8 |
| 1025 | F | CF₃ | Me | H | F | 8.3 | 528.1<br>530.1 |

What is claimed is:

1. A compound of the formula (I)

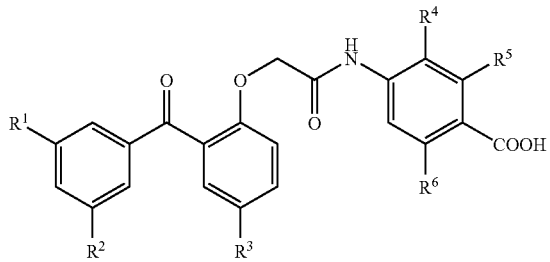

wherein,

R¹ and R² are each independently selected from H, halo, cyano, $(C_{1-4})$alkyl, $(C_{1-4})$haloalkyl, $(C_{2-4})$alkenyl, $(C_{2-4})$alkynyl and $(C_{3-6})$cycloalkyl;
with the proviso that when R¹ is H, R² cannot be H;
R³ is halo;
R⁴ is selected from $(C_{1-4})$alkyl, halo and nitro; and
R⁵ and R⁶ are each independently selected from H, halo and $(C_{1-4})$alkyl;
or a salt thereof.

2. A compound according to claim 1 wherein R¹ and R² are each independently selected from H, halo, cyano, $(C_{1-4})$alkyl, $(C_{1-4})$haloalkyl, and $(C_{3-6})$cycloalkyl; with the proviso that when R¹ is H, R² cannot be H.

3. A compound according to claim 2 wherein R¹ and R² are each independently selected from H, fluoro, chloro, bromo, cyano, trifluoromethyl and cyclopropyl; with the proviso that when R¹ is H, R² cannot be H.

4. A compound according to claim 1 wherein R³ is chloro.

5. A compound according to claim 1 wherein R⁴ is selected from chloro, bromo, nitro and methyl.

6. A compound according to claim 5 wherein R⁴ is chloro, bromo or methyl.

7. A compound according to claim 1 wherein R⁵ is H, fluoro, chloro or methyl.

8. A compound according to claim 1 wherein R⁶ is H or fluoro.

9. A compound according to claim 1 wherein
R¹ and R² are each independently selected from H, halo, cyano, $(C_{1-4})$alkyl, $(C_{2-4})$alkenyl, $(C_{2-4})$alkynyl and $(C_{3-6})$cycloalkyl; wherein said $(C_{1-4})$alkyl is optionally substituted with one to three halo substituents;
with the proviso that when R¹ is H, R² cannot be H;
R³ is halo;
R⁴ is selected from $(C_{1-4})$alkyl, halo and nitro;
R⁵ is selected from H and halo; and
R⁶ is H;
or a pharmaceutically acceptable salt thereof.

10. A compound according to claim 1 wherein
R¹ and R² are each independently selected from H, halo, cyano, $(C_{1-4})$alkyl, $(C_{1-4})$haloalkyl, and $(C_{3-6})$cycloalkyl;
with the proviso that when R¹ is H, R² cannot be H;
R³ is chloro;
R⁴ is chloro, bromo, nitro or methyl;
R⁵ is H, fluoro, chloro or methyl; and
R⁶ is H or fluoro.

11. A compound according to claim 1 wherein
R¹ and R² are each independently selected from H, fluoro, chloro, bromo, cyano, trifluoromethyl and cyclopropyl;
with the proviso that when R¹ is H, R² cannot be H;
R³ is chloro;

$R^4$ is chloro, bromo or methyl;
$R^5$ is H, fluoro, chloro or methyl; and
$R^6$ is H or fluoro.

12. A compound of the formula

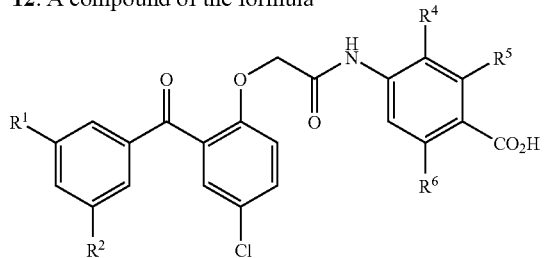

wherein $R^1$, $R^2$, $R^4$, $R^5$ and $R^6$ are as defined in the table immediately below.

| Cpd | $R^1$ | $R^2$ | $R^4$ | $R^5$ | $R^6$ |
|---|---|---|---|---|---|
| 1001 | F | CF$_3$ | Me | H | H; |
| 1002 | F | CF$_3$ | Me | F | H; |
| 1003 | F | CN | Me | F | H; |
| 1004 | F | cyclopropyl | Me | H | H; |
| 1005 | F | Cl | Me | H | H; |
| 1006 | H | CN | Me | H | H; |
| 1007 | F | CN | Me | H | H; |
| 1008 | F | CF$_3$ | Cl | H | H; |
| 1009 | F | CN | Cl | H | H; |
| 1010 | F | CF$_3$ | Cl | F | H; |
| 1011 | F | cyclopropyl | Me | F | H; |
| 1012 | F | Br | Me | F | H; |
| 1013 | F | Cl | Me | F | H; |
| 1014 | F | Br | Me | H | H; |
| 1015 | H | Br | Me | H | H; |
| 1016 | H | Br | Me | F | H; |
| 1017 | H | CN | Me | F | H; |
| 1018 | Cl | CN | Me | H | H; |
| 1019 | F | cyclopropyl | Br | H | H; |
| 1020 | F | CF$_3$ | Br | H | H; |
| 1021 | Cl | CN | Me | F | H; |
| 1022 | F | CF$_3$ | Cl | Cl | H; |
| 1023 | F | CF$_3$ | Me | Me | H; |
| 1024 | F | CF$_3$ | Me | Cl | H; or |
| 1025 | F | CF$_3$ | Me | H | F. |

13. A pharmaceutical composition, comprising a compound according to claim 1, or a pharmaceutically acceptable salt thereof, and one or more pharmaceutically acceptable carriers.

14. A composition according to claim 13 additionally comprising one or more other antiretroviral drugs.

15. A composition according to claim 14 wherein the one or more other antiretroviral drugs are selected from the group consisting of NRTIs, NNRTIs, protease inhibitors, entry inhibitors, integrase inhibitors, TAT inhibitors, maturation inhibitors, immunomodulating agents, antifungal agents and antibacterial agents.

16. A method of treating HIV infection in a human which comprises administering a therapeutically effective amount of a compound according to claim 1 or a pharmaceutically acceptable salt thereof.

* * * * *